United States Patent
Strocchia-Rivera

(10) Patent No.: US 9,116,038 B2
(45) Date of Patent: Aug. 25, 2015

(54) INTEGRATED OPTICAL ILLUMINATION REFERENCE SOURCE

(71) Applicant: International Business Machines Corporation, Armonk, NY (US)

(72) Inventor: Carlos Strocchia-Rivera, Highland, NY (US)

(73) Assignee: International Business Machines Corporation, Armonk, NY (US)

( * ) Notice: Subject to any disclaimer, the term of this patent is extended or adjusted under 35 U.S.C. 154(b) by 107 days.

(21) Appl. No.: 13/969,824

(22) Filed: Aug. 19, 2013

(65) Prior Publication Data

US 2015/0049336 A1   Feb. 19, 2015

(51) Int. Cl.
*G01J 1/08* (2006.01)
*F21V 13/04* (2006.01)
*F21V 5/00* (2006.01)

(52) U.S. Cl.
CPC . *G01J 1/08* (2013.01); *F21V 13/04* (2013.01); *F21V 5/00* (2013.01)

(58) Field of Classification Search
CPC .............. G01J 1/08; F21V 13/04; F21V 5/00
USPC ........ 356/445; 359/731, 645, 678; 250/201.5, 250/458.1
See application file for complete search history.

(56) References Cited

U.S. PATENT DOCUMENTS

| | | | | | |
|---|---|---|---|---|---|
| 5,159,495 | A * | 10/1992 | Hamblen | ...................... | 359/731 |
| 5,394,414 | A * | 2/1995 | Kozlovsky et al. | ............. | 372/22 |
| 5,731,577 | A * | 3/1998 | Tanitsu | ...................... | 250/201.5 |
| 6,480,456 | B1 * | 11/2002 | Kawamura et al. | ........... | 369/120 |
| 6,768,834 | B1 * | 7/2004 | Gruhlke | .......................... | 385/24 |
| 8,120,781 | B2 | 2/2012 | Liesener | | |
| 8,317,342 | B2 * | 11/2012 | Anderson | ..................... | 359/839 |
| 8,379,218 | B2 | 2/2013 | Deck et al. | | |
| 2004/0156043 | A1 * | 8/2004 | Toker et al. | ................. | 356/237.1 |
| 2006/0209424 | A1 * | 9/2006 | Shimo | .......................... | 359/678 |
| 2007/0205378 | A1 * | 9/2007 | Tomioka et al. | ........... | 250/458.1 |
| 2014/0043610 | A1 * | 2/2014 | Engel et al. | ................... | 356/369 |

FOREIGN PATENT DOCUMENTS

| | | | |
|---|---|---|---|
| JP | 2007248080 A | 9/2007 | |
| JP | 4611899 B2 | 1/2011 | |

* cited by examiner

*Primary Examiner* — Sang Nguyen
(74) *Attorney, Agent, or Firm* — Keivan Razavi; Catherine Ivers

(57) ABSTRACT

An integrated illumination reference source for generating an illumination reference signal may include an optical element having a first outer surface and a second outer surface, such that the first and the second outer surface are substantially opposing. The optical element receives an incident optical signal at the first outer surface and projects the incident optical signal from the second outer surface onto a surface. A reflective device that is located on a region of the second outer surface is offset from an optical axis of the optical element. The reflective device includes a reflective surface that reflects a portion of the incident optical signal from the second outer surface back through the first outer surface, whereby the reflective surface of the reflective device is encapsulated between the first outer surface and the second outer surface of the optical element.

8 Claims, 5 Drawing Sheets

INTEGRATED OPTICAL ILLUMINATION REFERENCE SOURCE

BACKGROUND a. Field of the Invention

The present invention generally relates to optical systems, and more particularly to providing reference illumination sources within such optical systems.

b. Background of Invention

Optical metrology and inspection equipment such as reflectometers may often use high power optical lens/objectives in close proximity to surfaces for measurement and/or inspection purposes. In manufacturing environments these surfaces may often release gases or vapors that can coat the lens/objectives in such a manner that light collected by these lens/objectives is distorted. The measurement and/or inspection results are thus distorted.

Metrology and inspection equipment may contain external illumination reflection reference surfaces which are assumed to be stable and used to control the illumination received by the lens/objectives. However, since these reference surfaces are also susceptible to released gases and vapors, the reference illumination levels generated by the reference surfaces become distorted. This distortion subsequently unduly influences the measurement or inspection of the surface.

It may, therefore, be advantageous, among other things, to generate reference illumination surfaces that are at least to some extent independent of contaminants associated with a system.

BRIEF SUMMARY

According to at least one exemplary embodiment, an integrated illumination reference source for generating an illumination reference signal may include an optical element having a first outer surface and a second opposing outer surface, whereby the optical element receives an incident optical signal at the first outer surface and projects the incident optical signal from the second outer surface onto a surface. The integrated illumination reference source may also include a reflective device that is located on a region of the second outer surface offset from an optical axis of the optical element, such that the reflective device has a reflective surface that reflects a portion of the incident optical signal from the second outer surface back through the first outer surface. The reflective surface of the reflective device is encapsulated between the first outer surface and the second outer surface of the optical element.

According to at least one other exemplary embodiment, a method of generating an illumination reference signal in an optical system used for providing reflectivity measurements from a surface under test is provided. The method may include receiving an optical signal for propagation through a plurality of optical elements and a final stage optical element, whereby the final stage optical element projects a first portion of the optical signal onto the surface under test. A reflective surface is formed that is encapsulated within a region of the final stage optical element and offset from an optical axis corresponding to the final stage optical element, such that the reflective surface reflects a second portion of the optical signal away from the surface under test. The reflected second portion of the optical signal is detected. A first magnitude value is then generated from the detecting of the reflected second portion of the optical signal, whereby based on the forming of the encapsulated reflective surface, a variation in the first magnitude value is independent of the final stage optical element.

According to at least one other exemplary embodiment, a computer-implemented method of determining measurement variance in an optical system used for providing reflectivity measurements from a surface under test is provided. The method may include generating, by a processor, a first plurality of magnitude values based on receiving a first reflected optical signal from a reflective surface integrated within a final stage optical element of the optical system; and generating, by the processor, a second plurality of magnitude values based on receiving a second reflected optical signal from the surface under test. The processor may also determine a variation corresponding to the generated first plurality of magnitude values, a variation corresponding to the generated second plurality of magnitude values, and total variance values based on the determined variation in both the first and the second plurality of magnitudes. The processor may then determine average measurements from the first and the second plurality of magnitude values and determine reflectivity measurements from these determined average measurements.

BRIEF DESCRIPTION OF THE SEVERAL VIEWS OF THE DRAWINGS

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1A:
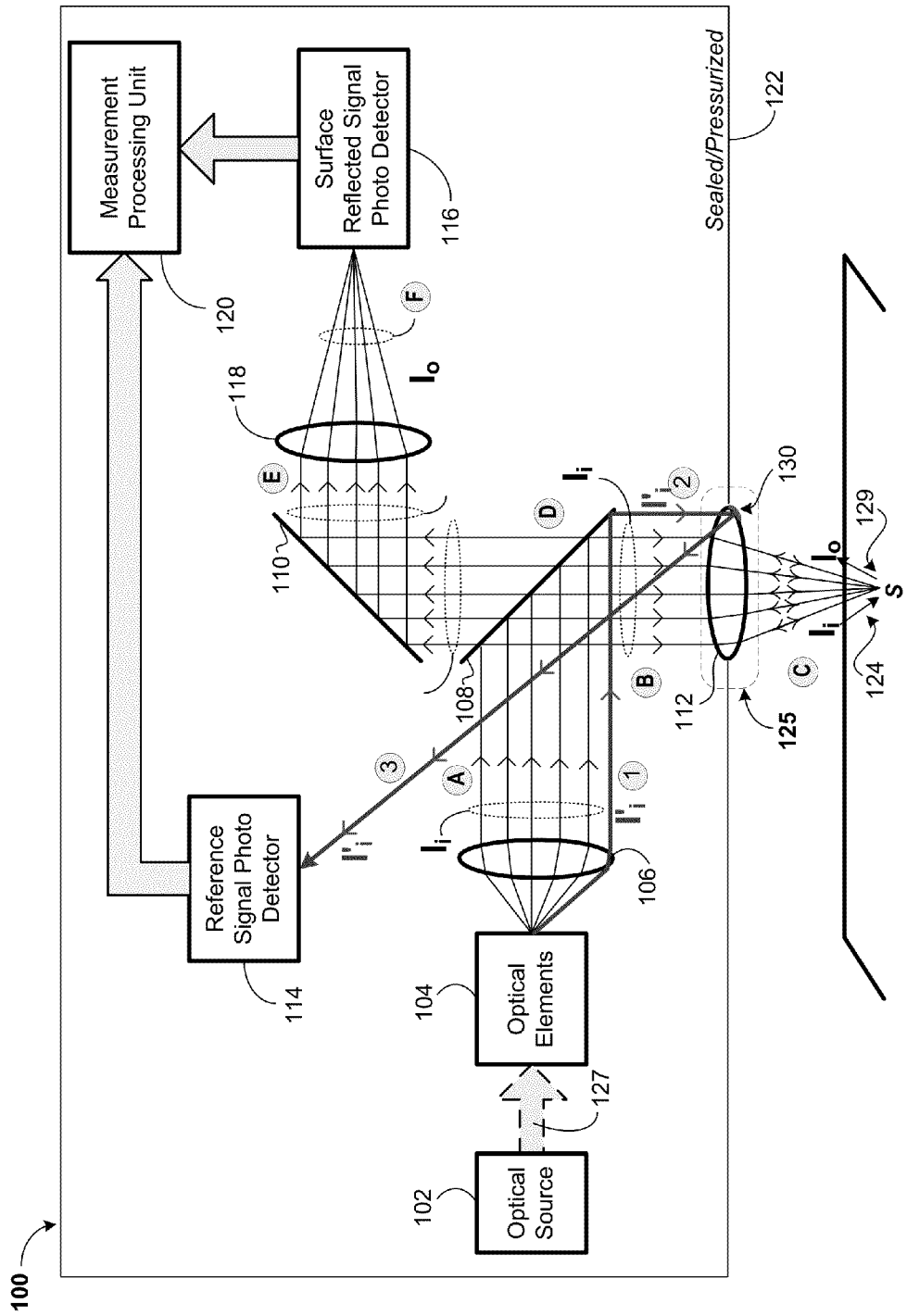
FIG. 1A is an optical system, according to one embodiment.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc. or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The following one or more exemplary embodiments describe, among other things, an optical reference surface utilized within an optical system that determines measurement errors that may be caused by internal characteristic changes (e.g., losses due to solarization) to the various optical components of the optical system.

Referring to FIG. 1, an embodiment of an optical system 100 such as a reflectometer is depicted. The optical system 100 may include an optical source 102, one or more optical elements 104 such as lenses, mirrors, splitters, etc., a collimating lens 106, a first splitter 108, a second splitter 110, a final stage optical element 112 such as a focusing lens, a reference signal photodetector 114, a surface reflected signal photodetector 116, a photodetector focusing lens 118, and a measurement processing unit 120. The above-mentioned components 102-120 of the optical system 100 may be housed in a sealed and pressurized enclosure 122 in order to protect these optical components from debris (e.g., gases) that may impact the measurements.

As depicted, a focused incident optical signal $I_i$, as indicated at 124, illuminates a surface under test S, whereby a reflected portion (i.e., from surface S) $I_o$, as indicated by 129, of the focused incident optical signal $I_i$ is used to determine the reflectivity characteristics of the surface under test S. For example, the surface under test S may include a film, dielectric, or any other layer associated with a device such as a manufactured semiconductor structure. By determining the reflectivity of such surfaces S, the characteristics and/or manufacturing tolerances of the films, dielectrics, or other layers may be determined.

In operation, the optical source 102 (e.g., arc lamp, incandescent lamp, fluorescent lamp, etc.) generates an optical signal that may have a wavelength anywhere between ultraviolet (UV) and near infrared (IR) wavelengths, depending on system application. The optical signal output from optical source 102 propagates along path 127 and is received by the one or more optical elements 104 such as lenses, mirrors, splitters, etc. As the optical signal traverses through the one or more optical elements 104, it is received by collimating lens 106. At the collimating lens 106, the incident optical signal, as indicated by $I_i$, is directed towards the beam splitter 108 (Path A), such that the beam splitter 108 reflects the collimated incident optical signal $I_i$ down onto the final stage optical element 112 (Path B), which may, for example, include a focusing lens. Thus, the final stage optical element 112 generates a focused incident optical signal $I_i$ at the surface under reflectivity test S (Path C).

The surface under test S illuminated by the focused incident optical signal $I_i$ may then, based on its characteristic reflectivity (R), reflect anywhere between approximately all (total reflection) to approximately none (total absorption) of the focused incident optical signal $I_i$ at surface S back towards the final stage optical element 112 as a reflected optical signal $I_o$ (Path C). The final stage optical element 112 may then collimate the reflected optical signal $I_o$ from surface S back towards the beam splitter 108 (Path B). At beam splitter 108, the reflected optical signal $I_o$ propagates through the beam splitter 108 (Path D) and onto beam splitter 110. Beam splitter 110 subsequently directs reflected optical signal $I_o$ onto the photodetector focusing lens 118 (Path E) for focusing (Path F) onto the active area of the surface reflected signal photodetector 116. The surface reflected signal photodetector 116 then converts the optical intensity of the reflected optical signal $I_o$ to a magnitude value (i.e., voltage or current value) that is determinative of the detected optical intensity (i.e., power). The magnitude value output from the photodetector 116 is then transmitted to the measurement unit 120 for processing.

Also at the collimating lens 106, a portion of the incident optical signal, as indicated by $I'_i$, is directed towards the beam splitter 108 (Path 1), such that the beam splitter 108 also reflects the portion of the incident optical signal $I'_i$ down onto the final stage optical element 112 (Path 2), which may, for example, include a focusing lens. However, the final stage optical element 112 includes a reflective device 130 having a known reflective surface that reflects the portion of the incident optical signal $I'_i$ back through the final stage optical element 112 and away from the surface under reflectivity test S (Path 3). Since the reflective surface of the reflective device 130 is set to provide maximum reflection, the reflective surface may include a high reflectivity material such as aluminum, silver, or gold with known reflectivity. Region 125, which includes the final stage optical element 112 and reflective device 130, is further described below with the aid of an expanded view of region 125, as depicted in FIG. 1B.

Figure 1B:
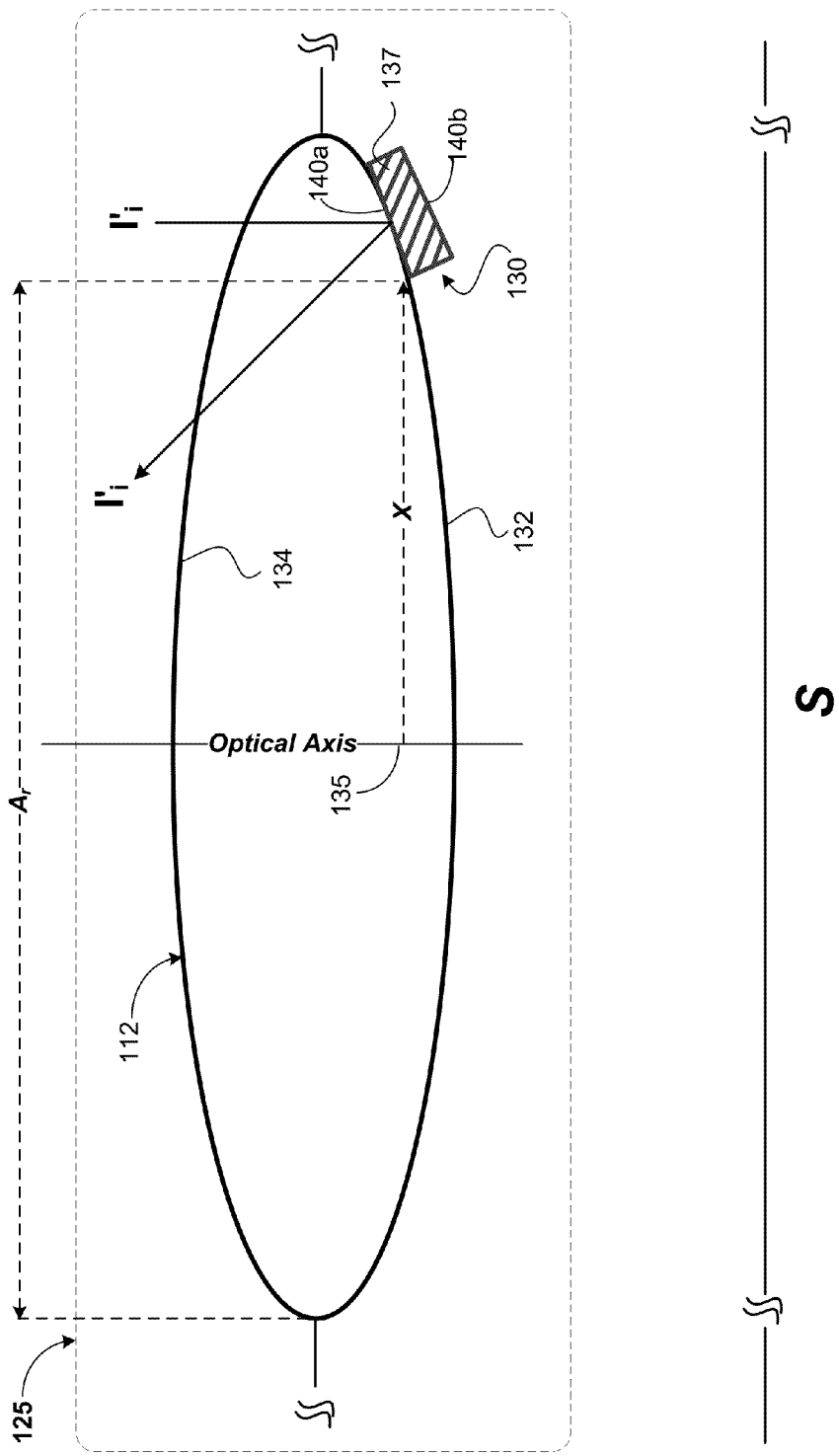
FIG. 1B is an expanded cross sectional view of an optical element having an integrated reflective surface that is used within the optical system of FIG. 1A, according to one embodiment.

As further shown in FIG. 1A, the portion of the incident optical signal $I'_i$ reflected back through the final stage optical element 112 by reflective device 130 (Path 3) is then received by the active area of the reference signal photodetector 114. The reference signal photodetector 114 then converts the optical intensity of the portion of the incident optical signal $I'_i$ to a magnitude value (i.e., voltage or current value) that is determinative of the detected optical intensity (i.e., power) based on the known reflectivity of reference device 130. The magnitude value output from the photodetector 114 is then transmitted to the measurement unit 120 for processing. The portion of the incident optical signal $I'_i$ detected by reference signal photodetector 114 acts a reference signal, whereby the ratio between the determined magnitude value corresponding to the reflected optical signal $I_o$ and the determined magnitude value corresponding to the portion of the incident optical signal $I'_i$ provides the reflectivity (R) measure of the surface under test S.

The portion of the incident optical signal $I'_i$ detected by reference signal photodetector 114 may be a predetermined/known percentage (e.g., 10%) of the total optical signal that is output from the optical source 102. Therefore, during the calibration of the optical system, this portion (i.e., 10%) of the incident optical signal $I'_i$ detected by the reference signal photodetector 114 may be accordingly weighted (i.e., 90%) to be in proportion with incident optical signal $I_i$ that is applied to surface S. In some implementations, the weighting may be achieved by amplifying the output of photodetector 114 using known photoreceiver circuitry. In other implementations, the weighting may be achieved by the measurement processing unit 120 prior to calculating the reflectivity value (R).

However, during the determination of the reflectivity (R) measure of the surface under test S, there may be a degree of uncertainty leading to a variation in power associated with the measured magnitude of the reflected optical signal $I_o$ and the measured magnitude of the portion of the incident optical signal $I'_i$. For example, due to uncertainties associated with signal loss changes over time (e.g., based on temperature fluctuations, solarization, debris, misalignment etc.) that may be imposed by beam splitters 108 and/or 110, the measured magnitude of the reflected optical signal $I_o$ associated with surface S may deviate from its actual value.

Similarly, due to uncertainties associated with signal loss changes over time (e.g., based on temperature fluctuations, solarization, debris, misalignment, component aging, etc.) that may be imposed by, for example, beam splitter 108, collimating lens 106, the one or more optical elements 104, and/or optical source 102, the measured magnitude of the portion of the incident optical signal $I'_i$ serving as an optical reference signal may deviate from its actual value. Since the reflective device 130 is located at the last stage to reflect back the portion of the incident optical signal $I'_i$ (the optical reference signal), it may be advantageous for the reflective device 130 to provide a reflective surface that is independent of any characteristic changes (e.g., loss) that could apply to the final stage optical element 112. Thus, in this case, any deviations in optical power associated with the portion of incident optical signal $I'_i$ (the optical reference signal) may be attributed to any one of the components (i.e., 102-108) that are upstream from the final stage optical element 112.

As illustrated in FIG. 1B, the reflective device 130 is integrated with the final stage optical element 112 in a manner that mitigates any contamination associated with the reflective device. By removing or reducing such contaminations that can add uncertain variations to the reflectivity R calculation, the reflective device 130 provides a degree of measurement confidence that identifies any upstream fluctuations in power that results from the optical system components and not the reflectivity device 130 itself. As depicted, reflective device 130 is formed on outer surface 132 of the final stage optical element 112, whereby outer surface 132 faces the surface under test S. The reflective device 130 is also formed at a region offset X from the optical axis 135 of the final stage optical element 112. By offsetting X the reflective device 130 relative to the optical axis 135, the majority of the lens area, as indicated by $A_r$, may be devoted to focusing the incident optical signal $I_i$ onto surface S. The reflectivity device 130 includes a reflective surface layer 137 having top and bottom opposing surfaces 140a, 140b. The top surface 140a of the reflective surface layer 137 is deposited on outer surface 132 of the final stage optical element 112, such that top surface 140a is encapsulated between outer surfaces 132 and 134, while bottom surface 140b of the reflective surface layer 137 remains exposed to the surface under test S. Since the top surface 140a is encapsulated between outer surfaces 132 and 134, it is shielded from debris and contamination that may result from, for example, the surface under test S. Moreover, outer surface 134 of the final stage optical element 112 is enclosed in a sealed and/or pressurized enclosure. In contrast, the bottom surface 140b of the reflective surface layer 137 that is exposed to the surface under test S may become contaminated by gases that may be released from surface S. This, however, does not affect the reflectivity of top surface 140a, which as depicted, reflects the portion of the incident optical signal $I'_i$ from the outer surface 132 of the final stage optical element 112 back through opposing outer surface 134 of the final stage optical element 112.

Figure 2:
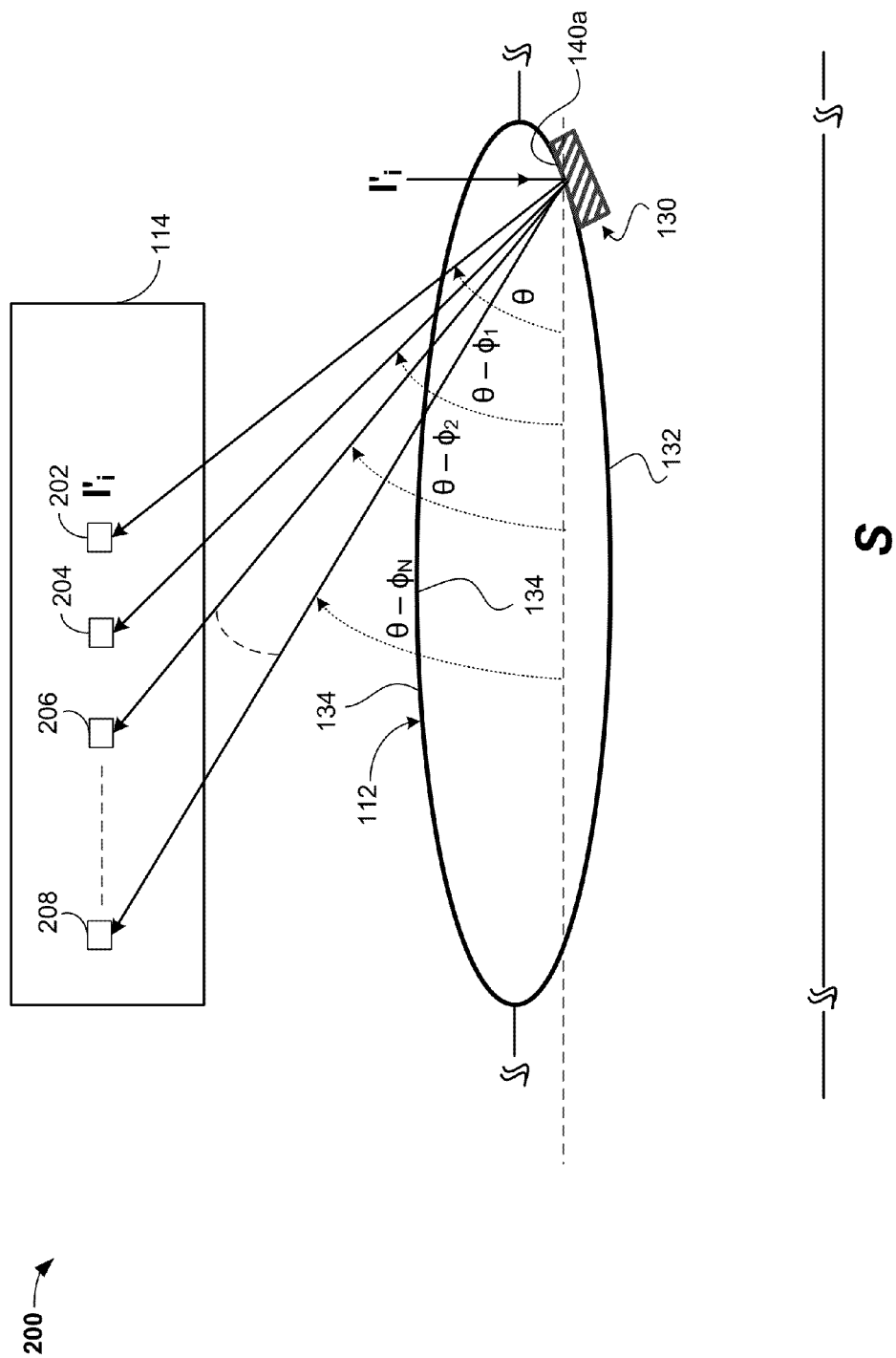
FIG. 2 illustrates detecting angular deviations in reflected reference signals for assessing conditions within the optical system, according to one embodiment.

FIG. 2 illustrates detecting angular deviations in the portion of the incident optical signal $I'_i$ serving as an optical reference signal for assessing optical component conditions within the optical system 100. For example, the reference signal photodetector 114 may include an array of photodetectors or a plurality of pixels 202-208. As previously described, the top surface 140a of reflective device 130 reflects the portion of the incident optical signal I'$_i$ from the outer surface 132 of the final stage optical element 112 back through opposing outer surface 134 of the final stage optical element 112. As depicted, the portion of the incident optical signal I'$_i$ reflected through the opposing outer surface 134 may be detected by pixel 202 under, for example, optimum/acceptable operating conditions exhibited by the optical system 100 (FIG. 1A). However, any distortion or alignment errors associated with the optical components 104, 106, 112 may deviate the propagation of the portion of the incident optical signal I'$_i$ reflected through the opposing outer surface 134 from angle θ to angle θ-φ$_1$. Thus, based on this angular deviation, the portion of the incident optical signal I'$_i$ reflected through the opposing outer surface 134 will now be detected by pixel 204. Similarly, distortion or alignment errors may cause the optical components 104, 106, 112 to further deviate the propagation of the portion of the incident optical signal I'$_i$ reflected through the opposing outer surface 134 between angle θ to angles θ-φ$_2$-θ-φ$_N$ based on which pixel (e.g., pixels 206-208) receives I'$_i$. Using the position of the pixel that detects I'$_i$, the angular deviation may be geometrically determined. The angular deviation may then be correlated with the amount of distortion associated with one or more of the optical components 104, 106, 112. For example, a heating of the final stage optical element 112 may cause some distortion in the lens. Such distortion may subsequently divert the I'$_i$ the signal. Generally, for example, such angular deviations may be caused by optical path changes, the cause of which may include the heating of optical elements.

Figure 3:
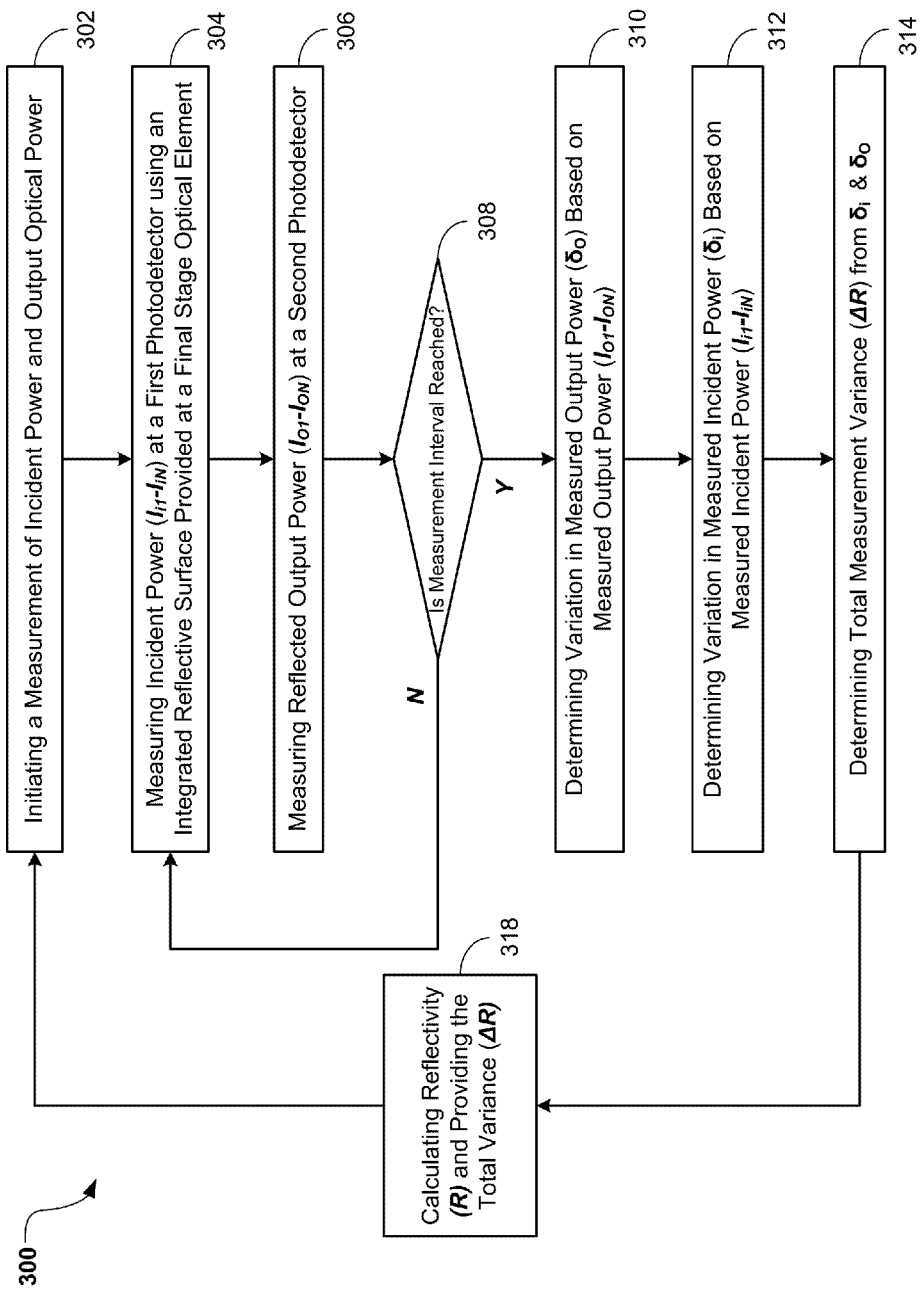
FIG. 3 is a flow chart for determination measurement variance and reflectivity in the optical system of FIG. 1A, according to one embodiment.

FIG. 3 is a flow chart 300 for determination measurement variance in the optical system of FIG. 1A, according to one embodiment. The process of flow chart 300 may be described with the aid of FIG. 1A. Moreover, the process of flow chart 300 may be implemented as an executable program within measurement processing unit 120 (FIG. 1A). The process of flow chart 300 may, therefore, also be defined as optical signal processing program 300.

Referring to FIG. 3, at 302, the measurement of incident optical power using the portion of the incident optical signal I'$_i$ serving as an optical reference signal is initiated by activation of optical source 102 (FIG. 1A). Also at 302, the measurement of reflected optical output signal I$_o$ (Path F) is also initiated. For example, the optical source 102 (FIG. 1A) may generate an optical signal for illuminating the surface under test S for a time interval in the range of about 1-10 seconds. Thus, this time interval may be the measurement interval over which the portion of the incident optical signal I'$_i$ and the reflected optical output signal I$_o$ (Path F) are measured.

At 304, the portion of the incident optical signal I'$_i$ serving as an optical reference signal (FIG. 1A: Path 3) is reflected from reflective device 120 of the final stage optical element 112 and detected by reference signal photodetector 114 (FIG. 1A). Based on the detected portion of the incident optical signal I'$_i$, the measurement processing unit 120 (FIG. 1A) then determines the incident optical power I$_i$ (FIG. 1A: Path C) that illuminates the surface under test S. The measurement processing unit 120 (FIG. 1A) may sample and determine multiple magnitude values for the incident optical power I$_i$ (FIG. 1A: Path C). For example, within a measurement interval of 1 second, three measurements (I$_{i1}$, I$_{i2}$, I$_{i3}$) may be made, whereby, I$_{i1}$=55 W, I$_{i2}$=60 W, and I$_{i3}$=65 W. It may be appreciated that for illustrative brevity three values are described. However, over the measurement interval of 1 second, a multitude of values may be obtained (e.g., 100-1000 measurements).

At 306, the reflected optical output signal I$_o$ (FIG. 1A: Path F) from the surface under test S (FIG. 1A) is detected by surface reflected signal photodetector 116 (FIG. 1A). The reflected optical output signal I$_o$ (Path F) is then determined by the measurement processing unit 120 (FIG. 1A). The measurement processing unit 120 (FIG. 1A) may sample and determine multiple magnitude values for the reflected optical output signal I$_o$ (FIG. 1A: Path F). For example, within the measurement interval of 1 second, three measurements (I$_{O1}$, I$_{O2}$, I$_{O3}$) may be made, whereby, I$_{O1}$=25 W, I$_{O2}$=30 W, and I$_{O3}$=35 W. The reflected optical output signal I$_o$ (FIG. 1A: Path F) and the incident optical power I$_i$ (FIG. 1A: Path C) are measured simultaneously during the measurement interval. It may be appreciated that for illustrative brevity three values are described. However, over the measurement interval of 1 second, a multitude of values may be obtained (e.g., 100-1000 measurements).

At 308, it may be determined whether the measurement interval (e.g., 1 second) has been reached. If not, more magnitude values for the reflected optical output signal I$_o$ (FIG. 1A: Path F) and incident optical power I$_i$ (FIG. 1A: Path C) are determined by the measurement processing unit 120 (FIG. 1A). In the above example, three (3) measurements for each are determined. If the measurement interval has been reached, the process moves to 310. The measurement interval may be predetermined and based on how long the optical source 102 (FIG. 1A) illuminates the surface under test S. As described above, this interval may be set to be, for example between 1-10 seconds.

At 310, a variation (δ$_O$) in the reflected optical output signal I$_o$ (Path F) determined by the measurement processing unit 120 (FIG. 1A) is calculated. Based on the above example, within the measurement interval of 1 second, the three measurements were determined to be: I$_{O1}$=25 W, I$_{O2}$=30 W, and I$_{O3}$=35 W. Thus, the average output power is I$_{AV\_O}$=30 W and the variance in output power is δ$_0$=±5 W (0.16=16%).

At 312, a variation (δ$_i$) in the incident optical power I$_i$ (FIG. 1A: Path C) determined by the measurement processing unit 120 (FIG. 1A) is calculated. Based on the above example, within the measurement interval of 1 second, the three measurements were determined to be: I$_{i1}$=55 W, I$_{i2}$=60 W, and I$_{i3}$=65 W. Thus, the average incident power is I$_{AV\_i}$=60 W and the variance in incident power is δ$_i$=±5 W (0.08=8%).

At 314, the measured total reflectivity variance (ΔR) may be calculated based on the determined δ$_i$ and δ$_O$ values, whereby:

$$\Delta R = R\sqrt{\left(\frac{\delta_0}{I_0}\right)^2 + \left(\frac{\delta t_i}{I_i}\right)^2} \quad \text{Equation (1)}$$

At 318, the reflectivity (R) may be calculated by $$\frac{I_{AV\_O}}{I_{AV\_i}} = \frac{30 \text{ W}}{60 \text{ W}} = 0.5\,(50\%)$$

and provided to the user of the optical system 100 (FIG. 1A), along with the total reflectivity variance (ΔR), as defined by Equation (1). The reflectivity (R) at each measurement interval may, therefore, be determined by taking the average values of the real-time measured incident power I$_i$ (304) and the real-time measured output power I$_o$ (306) during the measurement interval. This averaging may be accomplished by integrating the received optical signals at each of the photodetectors 114, 116 (FIG. 1A). The process of flow diagram 300 may then continue to generate different total variance ($\Delta R$) values for each time interval, which may enable the monitoring of any changes in total variance ($\Delta R$) that exceeds beyond a predetermined allowable variance (i.e., $\Delta R_{threshold}$). Once, for example, $\Delta R_{threshold}$ is exceeded, the optical system 100 (FIG. 1A) may be inspected in order to determine any potential causes (e.g., mechanical misalignments, etc.) of the changed variance.

As previously described, the measurement integrity of the system-based variance ($\delta_i$) is enhanced by the reflective device 130 (FIG. 1A) that is integrated with the last stage optical element 112, whereby any measurement variance defined by $\delta_i$ may be a function of the system component characteristic changes (e.g., losses) that are upstream of the last stage optical element 112. In some implementations, the process of flow diagram 300 may be utilized to track and analyze the system-based variance ($\delta_i$) over a predetermined time starting from when the system is calibrated. Following calibration, the optical components may be cleaned, tested, aligned, etc., in order to generate a particular optical reference signal $I'_i$ (FIG. 1A: Path 3) magnitude value (i.e., Watts) at the reference signal photodetector 114. Over the predetermined time, using the process of flow diagram 300, the measurement processing unit 120 may generate and log the system-based variance ($\delta_i$) for identifying performance degradation in the operation of one or more of the optical components (e.g., FIG. 1A: 102-108) that are upstream of the reflective device 130 (FIG. 1A). Therefore, potential component failures may be predicted.

Thus, the foregoing embodiments illustrate and describe, among other things, a reflective device 130 (FIG. 1A) that is integrated with a last stage optical element 112 such as a lens, whereby the lens 112 focuses an incident optical signal $I_i$ (FIG. 1A: Path C) onto a test surface S (FIG. 1A). The manner of integration of the reflective device 130 with the last stage optical element 112 maximizes the integrity (e.g., free from debris) of the generated optical reference signal $I_i$ (FIG. 1A: Path 3) in determining the actual incident optical signal $I_i$ (FIG. 1A: Path C) that is projected onto the test surface S (FIG. 1A). It may also be appreciated that the measurement processing unit 120 may factor the signal losses due to splitter 110 and focusing lens 118 during the determination of the reflected optical output signal $I_o$ (Path F) and, therefore, the reflectivity (R) measurement.

Figure 4:
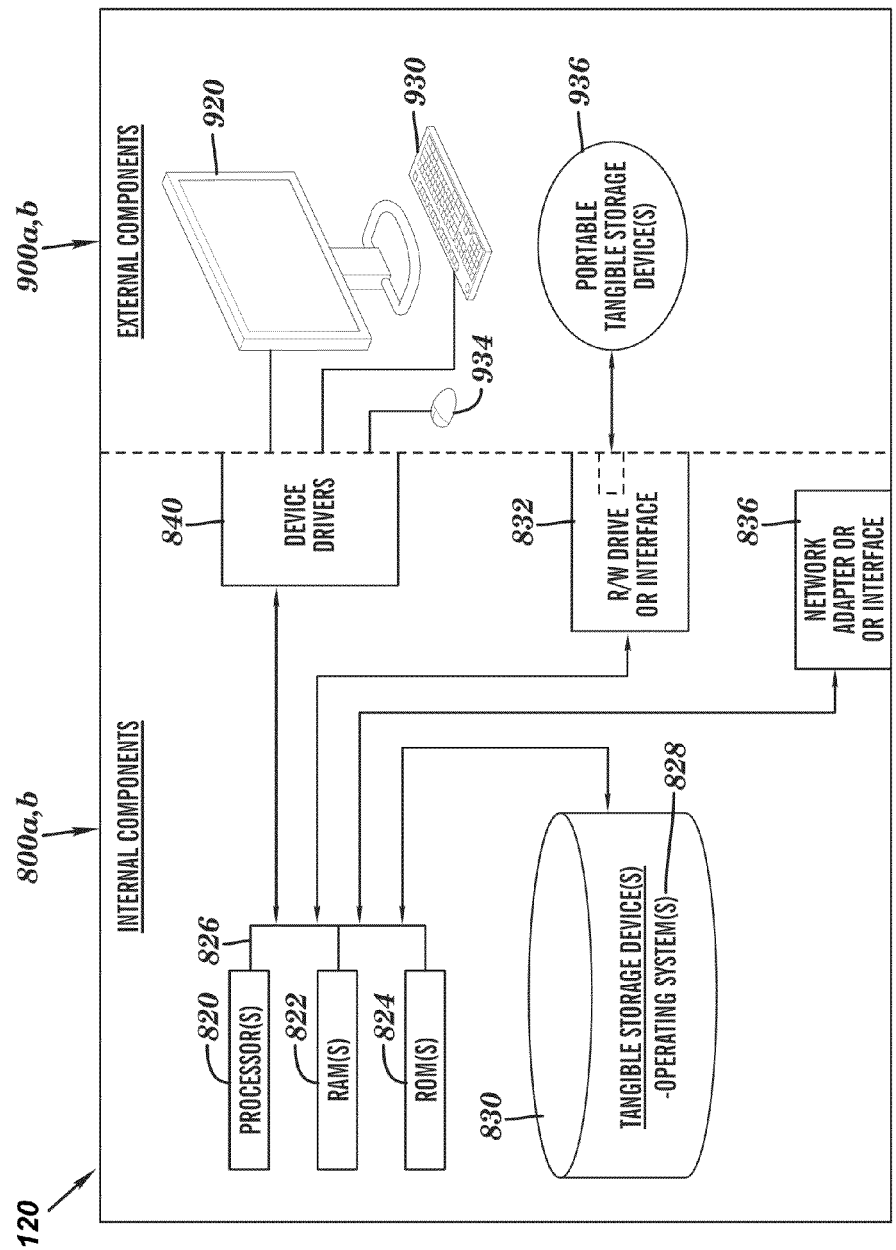
FIG. 4 is a block diagram of hardware and software within the measurement processing unit of FIG. 1, accordance to one embodiment.

FIG. 4 shows a block diagram of the components of a data processing system 800, 900, such as measurement processing unit 120 (FIG. 1A) in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 800, 900 is representative of any electronic device capable of executing machine-readable program instructions. Data processing system 800, 900 may be representative of a smart phone, a computer system, PDA, or other electronic devices. Examples of computing systems, environments, and/or configurations that may represented by data processing system 800, 900 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

Measurement processing unit 120 (FIG. 1A) may include respective sets of internal components 800 *a, b, c* and external components 900 *a, b, c* illustrated in FIG. 4. Each of the sets of internal components 800 *a, b, c* includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828 and programs in measurement processing unit 120 (FIG. 1A) is stored on one or more computer-readable tangible storage devices 830 for execution by one or more processors 820 via one or more RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800 *a, b, c* also includes a R/W drive or interface 832 to read from and write to one or more portable computer-readable tangible storage devices 936 such as a CD-ROM, DVD, memory stick, magnetic tape, magnetic disk, optical disk or semiconductor storage device. The optical system processing program 300 (FIG. 3) associated with measurement processing unit 120 (FIG. 1A) can be stored on one or more of the respective portable computer-readable tangible storage devices 936, read via the respective R/W drive or interface 832 and loaded into the respective hard drive 830.

Each set of internal components 800 *a, b, c* may also include network adapters (or switch port cards) or interfaces 836 such as a TCP/IP adapter cards, wireless wi-fi interface cards, or 3G or 4G wireless interface cards or other wired or wireless communication links. Optical system processing program 300 (FIG. 3), in measurement processing unit 120 (FIG. 1A), can be downloaded to measurement processing unit 120 (FIG. 1A) from an external computer (e.g., server) via a network (for example, the Internet, a local area network or other, wide area network) and respective network adapters or interfaces 836. From the network adapters (or switch port adaptors) or interfaces 836, the optical system processing program 300 (FIG. 3) associated with measurement processing unit 120 (FIG. 1A) is loaded into the respective hard drive 830. The network may comprise copper wires, optical fibers, wireless transmission, routers, firewalls, switches, gateway computers and/or edge servers.

Each of the sets of external components 900 *a, b, c* can include a computer display monitor 920, a keyboard 930, and a computer mouse 934. External components 900 *a, b, c* can also include touch screens, virtual keyboards, touch pads, pointing devices, and other human interface devices. Each of the sets of internal components 800 *a, b, c* also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Aspects of the present invention have been described with respect to block diagrams and/or flowchart illustrations of methods, apparatus (system), and computer program products according to embodiments of the invention. It will be understood that each block of the flowchart illustrations and/or block diagrams, and combinations of blocks in the flowchart illustrations and/or block diagrams, can be implemented by computer instructions. These computer instructions may be provided to a processor of a general purpose computer, special purpose computer, or other programmable data processing apparatus to produce a machine, such that instructions, which execute via the processor of the computer or other programmable data processing apparatus, create means for implementing the functions/acts specified in the flowchart and/or block diagram block or blocks.

The aforementioned programs can be written in any combination of one or more programming languages, including low-level, high-level, object-oriented or non object-oriented languages, such as Java, Smalltalk, C, and C++. The program code may execute entirely on the user's computer, partly on the user's computer, as a stand-alone software package, partly on the user's computer and partly on a remote computer, or entirely on a remote computer or server. In the latter scenario, the remote computer may be connected to the user's computer through any type of network, including a local area network (LAN) or a wide area network (WAN), or the connection may be made to an external computer (for example, through the Internet using an Internet service provider). Alternatively, the functions of the aforementioned programs can be implemented in whole or in part by computer circuits and other hardware (not shown).

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the one or more embodiment, the practical application or technical improvement over technologies found in the marketplace, or to enable others of ordinary skill in the art to understand the embodiments disclosed herein.

What is claimed is:

1. An integrated illumination reference source for generating an illumination reference signal comprising:
    an optical element located at a last stage of a sealed optical system having a plurality of optical components, the plurality of optical components located upstream of the optical element, the optical element having a first outer surface and a second outer surface, the first and the second outer surface being substantially opposing, wherein the optical element receives an incident optical signal at the first outer surface and projects the incident optical signal from a first region of the second outer surface onto a surface under reflectivity test that is located external to the sealed optical system, the surface under reflectivity test facing the second outer surface and reflecting a first portion of the projected incident optical signal received from the second outer surface back towards the second outer surface; and
    a reflective device that is located on a second region of the second outer surface offset from an optical axis of the optical element, the reflective device having a reflective surface that reflects a second portion of the incident optical signal from the second region of second outer surface back through the first outer surface, the first region of the second outer surface including a lens area for only transmitting the incident optical signal onto the surface under reflectivity test and transmitting the reflected first portion of the projected incident optical signal received form the surface under reflectivity test back towards the plurality optical components located upstream of the optical element, the second region of the second outer surface including a lens area for only reflecting the second portion of the incident optical signal as a reference optical signal,
    wherein the reflective surface of the reflective device is encapsulated between the first outer surface and the second outer surface of the optical element, the encapsulated reflective surface being contamination-free based on the reflective surface being shielded from contaminants released from the surface under reflectivity test, the contamination-free reflective surface used to determine reflectivity calculations that are independent of the released contaminants, and
    wherein fluctuations in the reference optical signal is based on optical power fluctuations caused by the plurality of optical components located upstream of the optical element, the reference optical signal being independent of any contamination associated with the last stage optical element facing the surface under reflectivity test.

2. The reference source of claim 1, further comprising:
    an optical source that generates the incident optical signal for propagation through a plurality of optical elements onto the surface via the optical element.

3. The reference source of claim 2, wherein the optical source comprises a lamp generating an optical signal ranging from ultraviolet to near infrared.

4. The reference source of claim 2, wherein the plurality of optical elements comprise at least a plurality of lenses.

5. The reference source of claim 1, further comprising:
    an optical detector that receives the portion of the incident optical signal reflected by the reflective surface from the second outer surface back through the first outer surface.

6. The reference source of claim 1, wherein the reflective device comprises a layer of deposited aluminum.

7. The reference source of claim 1, wherein the reflective device comprises a layer of deposited silver.

8. The reference source of claim 1, wherein the optical element comprises an optical lens.

* * * * *